United States Patent [19]

Adcock

[11] Patent Number: 4,959,133
[45] Date of Patent: Sep. 25, 1990

[54] FIELD INVERSION ELECTROBLOTTING & ELECTROELUTION

[75] Inventor: Mark W. Adcock, Guilford, Conn.

[73] Assignee: Eastman Kodak Company, Rochester, N.Y.

[21] Appl. No.: 299,868

[22] Filed: Jan. 23, 1989

[51] Int. Cl.⁵ .................. G01N 27/28; G01N 27/26; B01D 57/02
[52] U.S. Cl. ......................... 204/182.8; 204/299 R; 204/301; 204/180.1
[58] Field of Search .............. 204/299 R, 301, 180.31, 204/182.8

[56] References Cited

U.S. PATENT DOCUMENTS

| | | | |
|---|---|---|---|
| 4,181,594 | 1/1980 | Rizk et al. | 204/299 R |
| 4,576,702 | 3/1986 | Peck et al. | 204/299 R |
| 4,622,124 | 11/1986 | Kreisher et al. | |
| 4,737,251 | 4/1988 | Carle et al. | |
| 4,740,283 | 4/1988 | Laas et al. | |

Primary Examiner—John F. Niebling
Assistant Examiner—John S. Starsiak, Jr.
Attorney, Agent, or Firm—Dana M. Schmidt

[57] ABSTRACT

There are disclosed means and a method for electroblotting or electroelution, wherein a field is inverted repeatedly over time, until an electrophoretically separated DNA, RNA or protein is forced out of the gel and to an appropriate receiver by the net field so produced.

2 Claims, 2 Drawing Sheets

FIELD INVERSION ELECTROBLOTTING & ELECTROELUTION

FIELD OF THE INVENTION

This invention pertains to apparatus for the transfer of DNA, RNA or protein via an electric field to a membrane or salt trap.

BACKGROUND OF THE INVENTION

U.S. Pat. No. 4,622,124 describes an improved horizontal electroblotter used to transfer electrophoretically resolved DNA, RNA or protein from a gel to a receiver such as a membrane. The membrane is a more suitable recording medium to preserve the results of the separation. In this electroblotting process, the gel and membrane are placed in contact in a buffer, between a pair of electrodes, and a direct current is imposed by charging the electrodes with $+V$ and $-V$. The sign of the charge for each electrode is selected so that the sign on the electrode adjacent to the gel is the same as the net sign of the DNA, RNA or protein to be transferred. In this fashion, the charged DNA, RNA or protein is forced to transfer to the membrane. No attempt is made to reverse the charge on the electrodes.

This process works quite well, as long as the molecular weight of the DNA, RNA or protein is not too large. However, for molecular weights larger than about $2 \times 10^4$ base pairs, the direct field approach is not adequate to dislodge the high molecular weight material from the gel, at least not in reasonable lengths of time (less than one day).

In addition to transfer via electroblotting, a related transfer process is electroelution, in which there is no need to maintain the DNA, RNA or protein in a specified record of separation. Instead, the DNA, for example, has already been identified, and is needed to be extracted so that it can be purified or cloned. In such cases it is transferred from the gel to a receiver such as a dialysis cup membrane or a salt trap, for example as described in U.S. Pat. No. 4,576,702. In such a case, both the receiver and the gel are placed in a buffer bath so that they are between two electrodes, and a direct current is imposed by charging the two electrodes substantially as described above for electroblotting. Again, such electroelution processes work efficiently only if the molecular weights to be transferred are less than about $2 \times 10^4$ base pairs.

Chemical elutions have also been tried, in which the gel is melted and the DNA, RNA or protein is extracted by an aqueous phase-oil phase separation. This has proven unsatisfactory, however, as mixing is an essential step in that process, and the mixing leads to shear stress that shears the DNA, RNA or protein unacceptably.

Therefore, there has been a need prior to this invention to provide an electroblotting and/or electroelution process, and apparatus therefore, that can effectively transfer the larger molecular weight DNA, RNA or protein to a suitable receiver.

It has been found that such larger molecular weight materials can be moved within gel for purpose of electrophoretic separation, by altering the fields imposed upon the pair of electrodes, so that the field changes direction. Examples include the processes described in U.S. Pat. No. 4,740,283 and U.S. Pat. No. 4,737,251. However, neither of these patents suggests the use of field changes as a means of bringing about transfer out of the gel. More specifically, the '283 patent, when ready to transfer by electroblot, provides for a direct current flow in only one direction, FIG. 5, just as has always been done in electroblotting, even though the rest of the patent deals with fields that alternate in direction for moving the large molecules through the gel.

SUMMARY OF THE INVENTION

I have determined that a process used to electrophoretically separate large molecules of DNA, RNA and protein within a gel, is also effective in electrotransferring such material from the gel to another receiver, unlike the teaching of the '283 patent.

More specifically, in accord with one aspect of the invention, there is provided a method of transferring separated nucleic acids or proteins from an electrophoresis gel to a receiver suitable for further processing. The method comprises the steps of (a) placing a gel with already-separated nucleic acids or proteins in contact with a buffer in which a suitable receiver is placed; (b) positioning two electrodes on opposite sides of the gel-buffer-receiver combination; (c) applying to one of the two electrodes for a time T1, a charge $+V1$, and on the other electrode a charge $-V1$, the electrode closest to the gel having a charge with the same sign as the net charge on the nucleic acid or the protein; (d) for a time T2 that is the same or different from time T1, placing a charge on the one and on the other electrodes of a value $-V2$ and $+V2$, respectively, where $|V1|$ and $|V2|$, and T1 and T2, are selected in magnitude to assure a net migration of the separated nucleic acid or protein from the gel to the membrane; and (e) repeating steps (c) and (d) until the transfer is complete. (The symbols $||$ mean the absolute value of the variable.) This method is useful both in electroblotting and electroelution.

In accord with another aspect of the invention, there is provided an apparatus for electrically transferring separated nucleic acids or proteins from an electrophoresis gel to a receiver. The apparatus comprises (a) means for holding a gel on which the acids or proteins have been separated, and a receiver for the acid or protein, the holding means including a tank suitable for holding a buffer liquid; (b) a pair of electrodes disposed within the holding means with the gel and the receiver positioned between the electrodes; (c) a voltage source for biasing either of the electrodes for a predetermined time with a predetermined voltage V1 or V2, the other of the electrodes being simultaneously charged with a $-V1$ or $-V2$, respectively; (d) switching means for alternately switching the voltage source between the electrodes, and for selecting the voltage from the value V1 or V2; and (e) control means for controlling the switching means in accord with a preselected pattern.

Accordingly, it is an advantageous feature of the invention that electroblotting or electroelution can be carried out even with DNA, RNA or protein larger in molecular weight than $2 \times 10^4$ base pairs.

It is another advantageous feature of the invention that some of the equipment used to cause electrophoretic separation of the substances in the gel is also useful in the transfer of the separated substances to another receiver.

Other advantageous features will become apparent upon reference to the description of the preferred embodiments, when read in light of the attached drawings.

DESCRIPTION OF THE PREFERRED EMBODIMENTS

Figure 1:
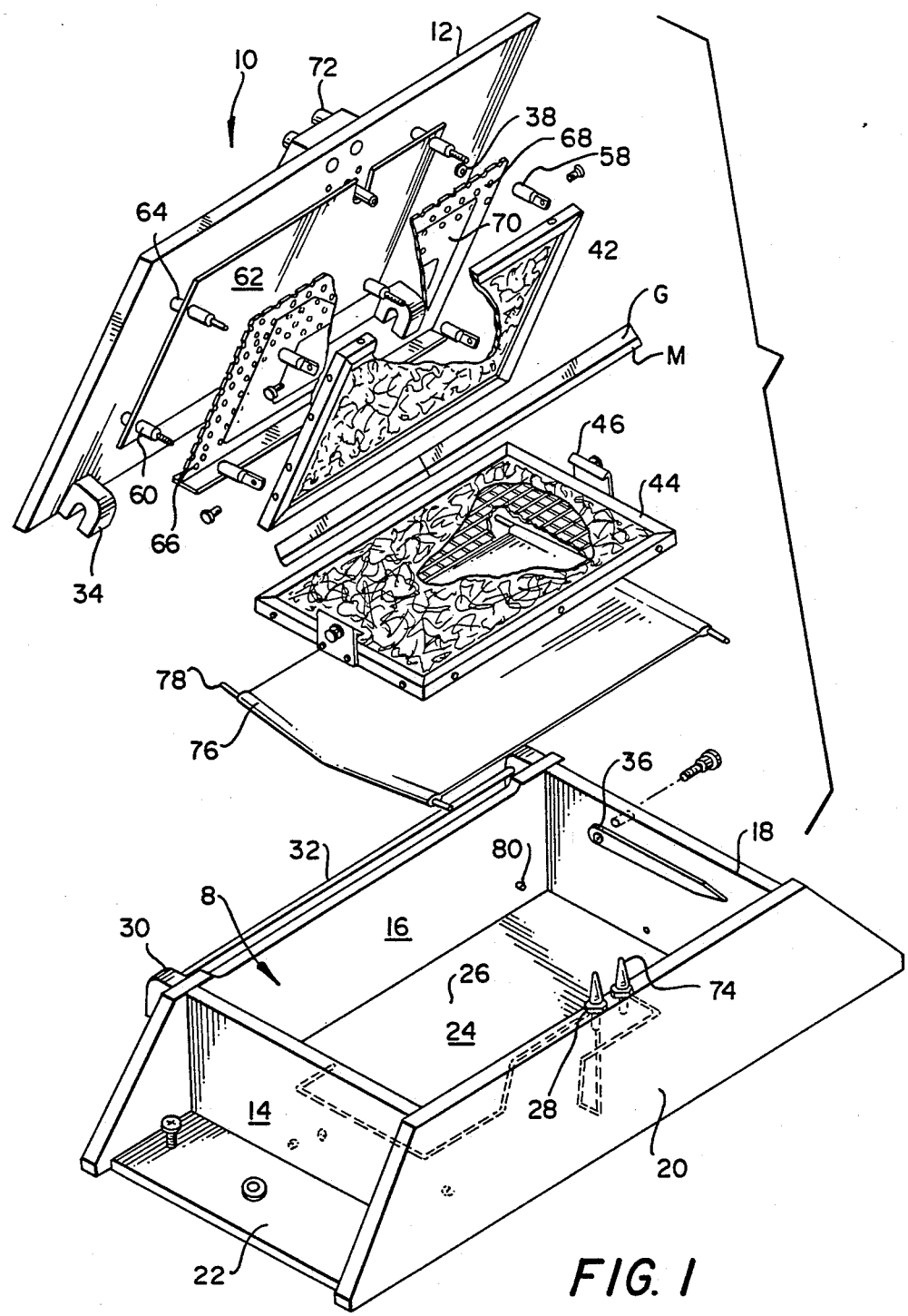
FIG. 1 is a partially exploded view in perspective of an electroblotting apparatus adapted to practice the invention.

I have constructed means and a method for operating electroblotting apparatus and electroelution apparatus so as to blot or elute, respectively, molecular weight DNA, RNA or protein which has been thought incapable of transfer using electrotransfer techniques. The preferred apparatus providing such means is discussed in terms of the electroblotting apparatus of U.S. Pat. No. 4,622,124 or the electroeluting apparatus of U.S. Pat. No. 4,576,702. In addition, the invention is useful with other apparatus capable of electrotransferring DNA, RNA, or protein from electrophoresis medium to a membrane.

As noted, a preferred electroblotting apparatus is that described in U.S. Pat. No. 4,622,124, also shown herein in FIG. 1. It comprises a holding tank 8 for receiving a gel G and a membrane M placed in contact with the gel, and a buffer liquid. The tank comprises opposing sidewalls 14, 18 and 16, 20, a bottom wall 24, and a top wall or cover 12 hinged to a rail 32 at hinges 34. Bottom wall 24 has an electrode 26 coiled thereon, which connects to an electrical connector 28. The electrode on the opposite side of the gel-membrane combination is electrode 70, mounted on a screen or plate 66. This electrode in turn connects to a connector 72. A baffle 76 is positioned between the gel-membrane combination to direct bubbles to the side to prohibit their accumulation on the supports for the gel-membrane combination G-M. Support 44 clamps to support 43 with the combination G-M sandwiched between the two supports.

A useful buffer for this electroblotter is as follows:

TAE Formulation 0.04 Molar Tris-acetate [Tris(hydroxymethyl)aminomethane acetate]
0.001 Molar EDTA [ethylenediamene-tetraacetic acid]
balance, water
pH=8.0 approximately The rest of the apparatus, and its use, are described in U.S. Pat. No. 4,622,124, the details of which are expressly incorporated herein by reference.

Alternatively, in some electroblotters the gel and membrane are held together by the electrodes themselves (not shown), and the buffer tank is omitted. This is possible because enough buffer remains in the gel to provide the needed buffer for the electrotransfer process.

Unlike the apparatus shown in U.S. Pat. No. 4,622,124, the control circuitry by which the field direction alteration is to be applied to the electroblotting or electroelution, is that which provides field inversion. That is, the circuitry described in U.S. Pat. No. 4,737,251, which teaches field inversion applied only to the electrophoresis, can be used, or the circuitry can be that described in U.S. Pat. No. 4,740,283. Apparatus in commercial use embodying such circuitry can be obtained under the trademark "DNA Star Pulse" sold by DNA Star, or the trademark "Geneline System" manufactured by Beckman Instruments, respectively. There is a significant difference, however—the power source providing the voltage and current of the field is not that used for the electrophoresis.

Figure 2:
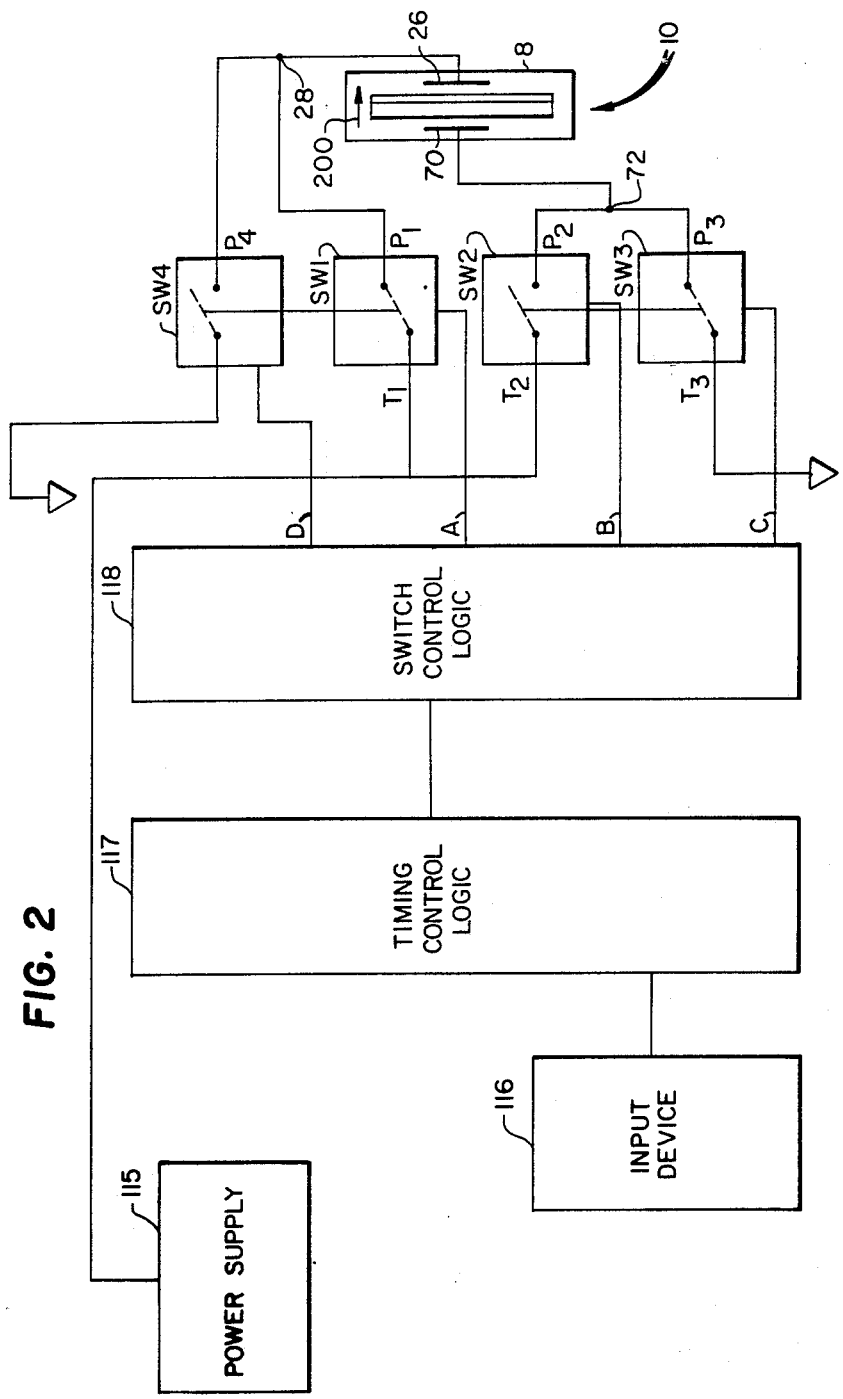
FIG. 2 is a simplified block diagram of the electrical controls useful in the electrotransfer apparatus that provides the switching of fields.

More specifically, useful circuitry is schematically shown in FIG. 2. This illustrates a suitable power supply 115 connected to one side of two solid state switching elements of SW1 and SW2 at points T1 and T2. If electroblotting is to be performed, such power supply preferably produces 140 volts and 0.5 to 2.5 amps of current. If electroelution is desired, the power supply is selected to produce 100 to 150 volts, at 20-30 milliamps, for example. The electroblotter of FIG. 1 is schematically shown as device 10 in FIG. 2. Electrode 26 and its connector 28 are wired to switches SW1 and SW4, which act as a double pole, double throw switch—either SW1 connects electrode 26 to voltage supply 115, or when the switch is thrown, SW4 connects it to ground. Similarly, electrode 70 and its connector 72 are wired to switches SW2 and SW3, also acting as a double pole, double throw switch and controlled to act simultaneously when SW1 and SW4 are switched. Thus, when as shown electrode 26 is connected via switch SW1 to power supply 115 to provide a voltage of +V, switch SW3 and electrode 70 are connected to ground. When all the switches are switched simultaneously, SW2 then connects electrode 70 to power supply 115 while switch SW1 and SW3 open and switch SW4 connects electrode 26 to ground. Switch control logic 118 serves to actuate the switches SW1-SW4. This control logic is driven by the timing control logic 117, which may consist of a commercially available sequence timer or programmable controller capable of producing logic level signals. A conventional input device 116 permits reprogramming of the timing control logic 117 by the user.

The rest of the circuitry can be constructed in accord with conventional techniques. Such circuitry can include conventional ramping means whereby the voltage +V or −V at any one time can be gradually changed (e.g., increased) before the polarity is reversed, or the value +V or −V can be varied each time it is applied in the "forward" or "reverse" direction.

The switch control logic must be operated to provide a net conductive force in the direction of arrow 200, FIG. 2. This is done by applying +V for a longer time to the one electrode 26 or 70 that is most likely to pull the DNA, RNA or protein away from the gel. Since most DNA and RNA have a net negative charge this means that +V from power supply 15 needs to be on electrode 26 longer than it is on electrode 70. For example, the voltage can be applied for 120 seconds to electrode 26, and then to electrode 70 for only 40 seconds.

The method of transfer, sometimes called "field inversion", will be readily apparent from the preceding description. The net migration to the receiver can be achieved by having a + voltage V1 on electrode 70 that is equal in magnitude to the minus voltage V1 on it previously applied, but for a shorter time period than the time that the minus voltage was applied. Or a minus voltage V2 can be applied that is less in magnitude than the plus voltage V1, for a time T2 that is equal to or less than the time T1 that the plus voltage is applied to electrode 70. Or still further, the minus voltage V2 on electrode 70 can be so much less, in magnitude, than the plus voltage V1, that the time of application T2 for −V2 is greater than the time of application T1 of +V1, since the magnitude differential of (V2−V1) still insures a net migration to the receiver. More particularly, in a preferred embodiment the transfer occurs by placing the gel along with the membrane as the appropriate receiver, in the tank 8 along with buffer; positioning the two electrodes on opposite sides of the gel-buffer-membrane combination; applying in the case of negatively charged DNA or RNA to electrode 26, a voltage $+V1$ while a $-V1$, is placed on electrode 70, for time T1 (e.g., 120 seconds); then for a time T2 that is less than T1, switching the charges so that electrode 70 has the voltage $+V1$ while electrode 26 has voltage $-V1$; and repeating the process until transfer is complete. Or alternatively, as described in U.S. Pat. No. 4,737,251, the same result can be achieved by applying a voltage $+V2$ to electrode 70, for an equal length of time T1, wherein the absolute value of V2 (hereinafter, $|V2|$) is less than $|V1|$. In such a case, a second voltage supply of lesser voltage is used, with switch SW2 and line T2 being connected to it rather than to power supply 15.

In still another embodiment, the appropriate receiver for the transfer is a salt trap and the apparatus is electroelution apparatus, exactly as is described in U.S. Pat. No. 4,576,702. The details of the '702 patent are expressly incorporated herein by reference. In such an apparatus, the gel and the receiver are not in contact like the gel and membrane of the electroblotter. The power supply and control of the switching is otherwise exactly as described for electroblotting albeit with a power supply providing a different level of voltage and current as noted above, so that the electroeluter of the '702 patent can be substituted for the electroblotter apparatus 10 of FIG. 2.

The invention has been described in detail with particular reference to preferred embodiments thereof, but it will be understood that variations and modifications can be effected within the spirit and scope of the invention.

What is claimed is:

1. A method of transferring separated nucleic acids or proteins from an electrophoresis gel to a membrane, comprising the steps of
   (a) placing a gel with already-separated nucleic acids or proteins in contact with a membrane to which the acids or proteins are to be transferred;
   (b) positioning the contacted gel and membrane between two oppositely disposed electrodes;
   (c) applying to one of said two electrodes for a time T1, a charge $+V1$, and on the other electrode a charge $-V1$, the electrode closest to said gel having the voltage with the same sign as the net charge on the nucleic acid or the protein;
   (d) for a time T2 that is the same or different from time T1, placing a charge on said one and on said other electrodes of a value $-V2$ and $+V2$, respectively, where $|V1|$ and $|V2|$, and T1 and T2, are selected in magnitude to assure a net migration of the separated nucleic acid or protein from the gel to the membrane; and
   (e) repeating steps (c) and (d) until the transfer is complete.

2. A method as defined in claim 1, wherein step (d) comprises using a positive voltage on the electrode farthest from the gel that is equal to or greater in magnitude for its application time, than the minus voltage applied to said farthest electrode, said positive voltage being equal in magnetude to said negative voltage only if the time of application of said negative voltage is less than that of the positive voltage.

* * * * *

UNITED STATES PATENT AND TRADEMARK OFFICE
CERTIFICATE OF CORRECTION

PATENT NO. : 4,959,133
DATED : September 25, 1990
INVENTOR(S) : Mark W. Adcock

It is certified that error appears in the above-identified patent and that said Letters Patent is hereby corrected as shown below:

Column 6, line 31, "magnetude" should read --magnitude--.

Signed and Sealed this

Twenty-fifth Day of February, 1992

Attest:

HARRY F. MANBECK, JR.

Attesting Officer

Commissioner of Patents and Trademarks